United States Patent [19]

Totten

[11] Patent Number: 4,601,719
[45] Date of Patent: Jul. 22, 1986

[54] SINGLE LEAFLET VALVE

[75] Inventor: Robert P. Totten, Diamond Springs, Calif.

[73] Assignee: Mitral Medical International, Inc., Denver, Colo.

[21] Appl. No.: 576,564

[22] Filed: Feb. 3, 1984
(Under 37 CFR 1.47)

[51] Int. Cl.[4] .............................................. A61F 2/24
[52] U.S. Cl. ..................................................... 623/2
[58] Field of Search ................... 3/1.5; 137/527, 527.8

[56] References Cited

U.S. PATENT DOCUMENTS

| | | | |
|---|---|---|---|
| 3,448,465 | 6/1969 | Pierce et al. | 3/1 |
| 3,737,919 | 6/1973 | Child | 3/1 |
| 3,825,957 | 6/1974 | Kaster | 3/1 |
| 3,953,898 | 5/1976 | Bloch | 3/1.5 |
| 4,021,863 | 5/1977 | Woien | 3/1.5 |
| 4,178,639 | 12/1979 | Bokros | 3/1.5 |
| 4,183,103 | 1/1980 | Bloch | 3/1.5 |
| 4,254,508 | 3/1981 | Bokros | 3/1.5 |
| 4,263,680 | 4/1981 | Reul et al. | 3/1.5 |
| 4,272,854 | 6/1981 | Bokros | 3/1.5 |
| 4,308,624 | 1/1982 | Klawitter | 3/1.5 |
| 4,326,304 | 4/1982 | Klawitter | 3/1.5 |
| 4,328,592 | 5/1982 | Klawitter | 3/1.5 |
| 4,357,715 | 11/1982 | Klawitter | 3/1.5 |
| 4,443,894 | 4/1984 | Klawitter | 3/1.5 |
| 4,451,937 | 6/1984 | Klawitter | 3/1.5 |

*Primary Examiner*—Richard J. Apley
*Assistant Examiner*—Alan W. Cannon
*Attorney, Agent, or Firm*—John E. Reilly

[57] ABSTRACT

A prosthetic heart valve is comprised of a low profile valve body defining a central orifice, and an occluder is supported within the valve body to pivot about an eccentric axis which is established by occluder-retaining means in the form of opposed, concave pocket members formed in inwardly projecting planar portions on the inner wall of the valve body. Lateral extensions on the occluder are insertable into the concave pocket members for movement between extreme limits which are established at least in part by limit stop elements directly associated with the pocket members and a rib portion on each of the lateral extensions. The novel and improved arrangement of the occluder retaining means enables a maximum range of movement while minimizing blood stagnation problems as well as stress and wear upon the valve elements.

14 Claims, 6 Drawing Figures

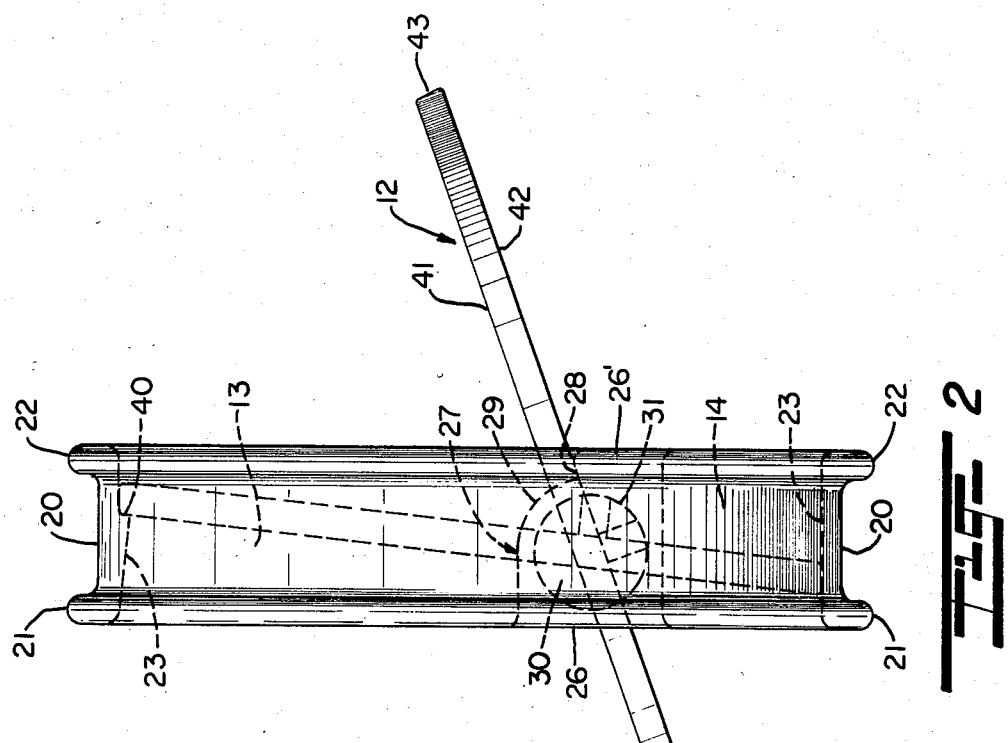
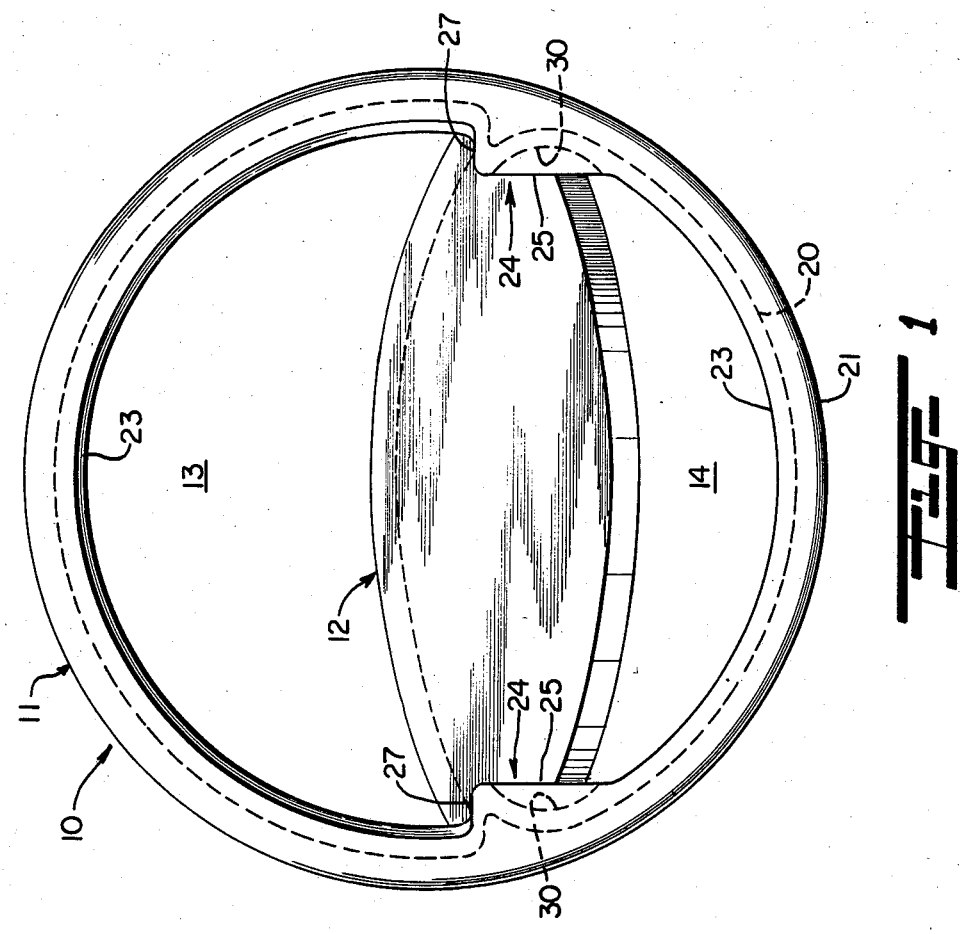

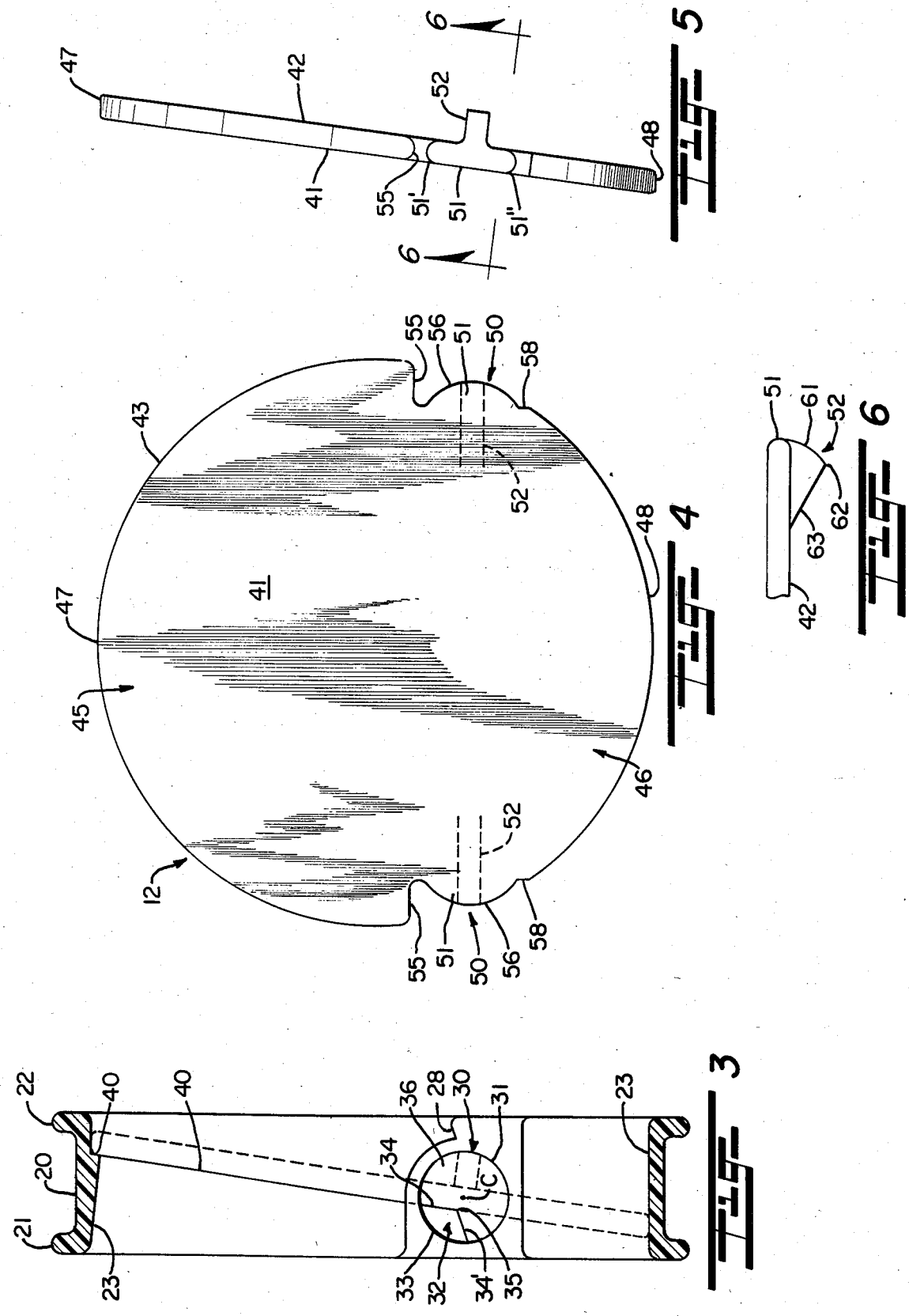

SINGLE LEAFLET VALVE

SPECIFICATION

This invention relates to heart valve prostheses; and more particularly relates to a novel and improved single leaflet valve which can be implanted as a replacement for defective natural heart valves.

BACKGROUND AND FIELD OF INVENTION

In the past, numerous variations of the single leaflet heart valve have been devised to the end of providing a valve which will simulate as closely as possible operations of natural heart valves. In earlier designs, for example, in the valve taught in U.S. Pat. No. 3,448,465 to W. S. Pierce et al, the leaflet or occluder is supported on and made to pivot about a fixed axis defined by a shaft or hinge member. Valves utilizing this type of leaflet support means have yielded fairly good results, and the principle is still represented in recent art, such as, U.S. Pat. Nos. 3,953,898 to E. Bloch and 4,263,680 to H. Reul et al. An inherent disadvantage in this type of valve is that blood tends to collect and stagnate around the fixed pivot point, causing the valve to stick.

Valves employing free-floating occluders have been devised in response to this problem. U.S. Pat. No. 3,737,919 to F. W. Child teaches a valve wherein a disk occluder pivots on a chordal axis between pivot members which project into the valve orifice, and which also rotates about its center during opening and closing. U.S. Pat. Nos. 4,183,103 to E. Bloch; 4,021,863 to A. Woien; and 3,825,957 to R. L. Kaster all are directed to occluders which are retained on and pivot about a guide post or strut extending into the central opening of the valve. Although such designs may be less susceptible than the earlier pivoting disk valves to blood stagnation and localized wear, a common drawback is that the disk-retaining guide members project or intrude sharply into the valve orifice, thereby obstructing the flow of blood therethrough. In certain other models the guide struts may extend substantially above the horizontal plane of the valve body; such high profile structures complicate implantation of the valve and tend to interfere with the ventricular septum resulting in aortic obstruction and low cardiac output.

At present, there remains a need for a pivotal, low profile single leaflet valve which provides maximum valve orifice while avoiding blood stagnation problems heretofore associated with pivoting disk valves.

SUMMARY OF THE INVENTION

It is therefore an object of the present invention to provide for a novel and improved artificial heart valve in which one or more leaflets or disks are movable to fully open and fully closed positions in response to the direction of fluid flow therethrough with a minimum of wear and stress upon the elements of the valve, the valve in the fully open position permitting substantially unrestricted flow of blood therethrough so as to minimize turbulence and promote laminar flow of the blood.

It is another object of the present invention to provide for a novel and improved single leaflet prosthetic heart valve in which the leaflet is so mounted as to avoid collection and stagnation of blood at the pivot points or axis of the leaflet while substantially eliminating projections extending from the valve body into the path of blood flow.

A further object of the present invention is to provide for a novel and improved pivoting disk heart valve in which the leaflet elements and the annular valve body are so constructed and arranged as to increase the effective orifice area or central opening of the valve with a minimal pressure gradient thereacross.

Another object of the present invention is to provide for a low profile, prosthetic heart valve which is long wearing and durable, quiet in operation with rapid response time, while employing a minimum number of parts and greatly simplifying manufacture of the valve.

Another object of the present invention is to provide a low profile valve body supporting a novel and improved leaflet having guide elements cooperating with recessed guide pockets in the valve body to establish optimum contact therebetween as the valve undergoes opening and closing; and further wherein the guide elements and guide pockets include cooperating means to prevent accidental release of the leaflets from the valve body.

In accordance with the present invention, there has been devised a novel and improved artificial heart valve comprising an annular valve body defining the center of a generally circular orifice or passageway and a generally flat occluder supported therein which pivots on an eccentric axis between an open position allowing blood flow through the passageway and a closed position preventing blood flow therethrough. The valve body is provided with occluder retaining means comprising a pair of opposed concave depressions or pocket members formed in inwardly projecting planar portions on the inner wall of the valve body, each pocket including an occluder limit stop member therein comprising a raised segment of the pocket. The occluder is provided with a pair of lateral extensions on opposite sides of the occluder for insertion into the corresponding concave pocket members for pivotal or swinging movement therein between side edges of the guide members. Each lateral extension is further provided with a transverse rib tapering along the occluder in a direction transverse to the pivotal movement of the lateral extension in the pocket member. The ribs are longitudinally curved to correspond to the concave configuration of the pocket members for pivotal movement therein. The aforesaid pockets on the inner wall of the valve body operate as limit stop means to engage the downstream surface of the occluder in the open position; in the closed position, the occluder seats along a ledge extending inwardly from the inner wall of the major portion of the valve body.

The above and other objects, advantages and features of the present invention will become more readily understood and appreciated from a consideration of the following detailed description of a preferred embodiment when taken together with the accompanying drawings in which:

BRIEF DESCRIPTION OF THE DRAWINGS

FIG. 1 is a plan view of an artificial heart valve in accordance with the present invention, as viewed from the downstream side of the valve;

FIG. 2 is a cross-sectional view taken about lines 2—2 of FIG. 1, with the occluder illustrated in the closed position in phantom line;

FIG. 3 is a cross-sectional view of the annular valve body with the occluder removed to show the configuration of the sockets and guide means;

FIG. 4 is a plan view of the occluder of the present invention;

FIG. 5 is a side view in elevation of the occluder illustrating the occluder pivot means; and FIG. 6 is a fragmentary cross-sectional view of the occluder taken along lines 6—6 of FIG. 5.

DETAILED DESCRIPTION OF THE PREFERRED EMBODIMENT

Illustrated in FIGS. 1 and 2 is an artificial heart valve 10 according to the present invention comprising an annular valve body 11 defining a generally circular valve orifice, and an occluder 12 is disposed in the valve body 11 for pivotal movement between an open and closed position in response to the flow of blood through the valve orifice. The occluder 12 is mounted for rotation about an eccentric axis so as to divide the circular valve orifice into major and minor orifices 13 and 14.

As illustrated in FIG. 2, the valve body 11 is generally channel-shaped in cross-sectional configuration so as to define an outer circumferential groove 20 adapted to receive a suture ring, not shown, in outer concentric relation thereto. The suture ring facilitates implantation of the valve into the heart, and may be of conventional construction. More specifically, the channel or groove 20 is defined by outwardly flaring upstream and downstream edges 21, 22 which are joined on the interior of the valve body by an inner wall surface 23.

Referring first to FIG. 1, it will be seen that the generally circular inner wall 23 is interrupted by a pair of opposed projections offset with respect to the diameter of the annular valve body 11 and intruding slightly into the valve orifice. As further illustrated in FIG. 1, the inner wall surface 23 on opposite sides of the minor orifice 14 is provided with straight portions 24 which project inwardly to form opposed flat facing surfaces 25 having upstream and downstream edge surfaces 26, 26' substantially coplanar with upstream and downstream edges 21, 22, respectively, of the valve body 11. Radially directed side edges 27 are disposed at approximate right angles to flat facing surfaces 25 to join the surfaces 25 with the curved inner wall surface 23. Each facing surface 25 has a concave socket or guide pocket 30 formed therein, to be described hereinafter in greater detail. Referring to FIG. 2, it will be seen that a portion 28 of the side edge 27 near the downstream edge 22 is longitudinally curved in a direction toward the major orifice 13. The side edge 27 is then curved further towards the major orifice 13, as at 29, so as to generally follow the configuration of a portion of the circumferential edge 31 of the pocket 30.

In the major orifice 13, the inner wall 23 is further provided with a narrow peripheral ledge 40 extending radially inwardly therefrom along the inner circumference of the major orifice between the straight portions 24 of the valve body 11. The ledge is inclined between the opposed straight portions 24 in a direction toward the downstream edge 22 of the valve body. Below the ledge 40 the inner wall 23 tapers to its original thickness at the upstream edge 21.

FIG. 3 illustrates the annular valve body 11 with the occluder 12 removed to more clearly show the guide pockets 30 and pivot guide means 32 associated therewith. Each guide pocket 30 is a generally spherical socket or depression formed in one of the flat facing surfaces 25 intermediate the upstream 21 and the downstream edge 22. Each guide pocket 30 defines an inner bearing surface 36 of uniform concavity except for leaflet guide means 32 which is a generally triangular segment in one quadrant of the pocket 30 and is raised with respect to the bearing surface 36 so as to be substantially planar with the flat facing surface 25 of the straight portion 24. The base 33 of the triangular guide means 32 comprises a portion of the circumferential edge 31 of the pocket 30, while side edges 34, 34' of the segment converge radially inwardly therefrom toward the center C of the spherical guide pocket 30, meeting to form apex 35 a spaced distance from the center C of the guide pocket.

Illustrated in FIG. 4 is a leaflet or occluder 12 adapted for mounting within guide pockets 30 of the annular body 11 for rotation on an eccentric or chordal axis between open and closed positions in response to reversals of fluid flow through the valve orifice. The occluder or leaflet 12 is of substantially planar, generally circular configuration, and essentially comprises opposed upstream and downstream surfaces 41, 42 joined by a common peripheral edge 43. The occluder is so dimensioned as to be capable of closing off the passageway defined by the annular valve body 11 when the occluder is seated in its closed position.

The occluder is provided along its peripheral edge with opposed pivot means 50 in the form of a pair of inset lateral ears 51 disposed on opposite sides of the occluder, and a transverse rib 52 on the downstream surface of each ear 51 extends radially inwardly toward the center of the occluder 12. The pivot means 50 in effect divides the occluder 12 into major and minor portions 45, 46, and the peripheral edge 43 into leading and trailing edges 47, 48, respectively. More particularly, the pivot ears 51 are formed by a sharp angulation of the peripheral edge 43 radially inwardly toward the center of the occluder 12 to form straight edges 55 which are substantially parallel to the pivot axis and are offset with respect to the diameter of the occluder 12 in the direction of the minor portion 46. The straight edges 55 are rounded in cross-section, as illustrated in FIG. 5, and merge into the ears 51 in the plane of the occluder 12. The outer edge 56 of the ear 51 can be characterized as generally arcuate with a radius of curvature substantially equal to that of the inner bearing surface 36 of the guide pocket 30, each ear 51 being transversely rounded between upstream and downstream surfaces 41, 42 of the occluder. Each ear 51 is dimensioned in length to be slightly less than the diameter of the guide pocket 30 and each terminates short of the trailing edge 48 where it is joined thereto by flat portion 58.

Referring to FIGS. 5 and 6, it will be seen that each pivot ear 51 is provided on its downstream surface with a narrow radial flange or rib 52. The rib 52 is disposed approximately at right angles to the ear 51 and is generally wedge-shaped in vertical section. A rounded outer portion 61 curves away from the ear in a direction transverse with respect to the eccentric pivot axis of the ears. At edge 62, the rib 52 angles sharply in the opposite direction toward the downstream surface 42 of the occluder 12 along a tapered portion 63.

FIG. 5 illustrates that the combined arrangement of the ear 51 and rib 52 creates a generally T-shaped pivot member 50, the rib 52 in effect forming the stem portion and the ear 51 providing a pair of oppositely directed arms 51', 51" extending therefrom. Each T-shaped pivot member 50 is inserted in its respective guide pocket 30 such that the ear 51 projects into and is seated within the pocket 30 and the arms 51', 51" of the T extend diametrically thereacross, the arcuate edge 54 of the ear 51 and the rounded portion 61 of the rib 52 being in facing engagement with the concave inner bearing surface 36 of the guide pocket 30. The ribs 52 as previously described extend in perpendicular relation to the ears 51; therefore, when the ear 51 is properly seated within the guide pocket 30, the rounded outer portion 61 of the rib 52 will engage the correspondingly curved inner bearing surface 36 of the pocket 30. The edge 62 of the rib 52 lies adjacent the circumferential edge 31 of the pocket 30 and approximately level with the surface 25 of straight portion 24 of the valve body.

Thus mounted, the occluder is capable of pivotal movement about the eccentric pivot axis defined by the offset placement of the pivot ears 51 and guide pockets 30 with respect to the diameter of the valve body 11. During valve operation in response to blood flow therethrough, the pivoting movement of the occluder 12 within the valve body 11 is positively guided and regulated by the above-disclosed occluder mounting arrangement in the following manner: When the occluder 12 is in the closed position, illustrated in dotted line in FIG. 2, the upstream surface of one arm 51' of ear 51 rests against side edge 34 of the leaflet guide means 32 and the leading edge 47 of the occluder 12 engages the inclined ledge 40 along the inner wall surface 53 of the valve body 11. The occluder in the closed position is disposed at an angle of approximately 30° with respect to the horizontal axis of the valve body. When blood flows under pressure into the heart and such pressure is applied to the upstream side 41 of the leaflet or occluder 12, and particularly against the major orifice portion 45 thereof, the opening pressure against the occluder 12 will cause the occluder to pivot about its pivot ears 51 within the guide pockets 30 in a downstream direction from the closed position to the open position illustrated in full in FIG. 2. As a result, the upstream surface of the pivot ear 51, or the opposite arm 51'' of the ear, is caused to engage the opposite side edge 34' of the triangular guide means 32 within the guide pocket 30 when the occluder is in the open position. More particularly, during opening of the valve under fluid pressure the ear 51 is caused to pivot on an eccentric axis in a downstream or clockwise direction as illustrated in FIG. 2, the arcuate edge 56 of the ear 51 sliding and pivoting across the complementarily curved inner bearing surface 36 of the guide pocket 30. The apex 35 of the guide means 32 acts as a pivot point; and the ear in effect "rocks" over the apex 35, alternately engaging the opposite side edges 34, 34' of the guide means. As the ear pivots and slides over the inner bearing surface 36 of the guide pocket 30, the rib 52 simultaneously slides on a generally arcuate path within the pocket, its intermediate edge 62 traveling along the circumferential opening edge 31 of the pocket 30 and its curved outer portion 61 sliding over the concave inner surface of the pocket 30.

As the occluder 12 pivots to the open position, the straight edges 55 of the peripheral edge 43 adjacent the ears at the same time travels over the curved portions of the side edges 29 on the valve body projections 24 until the edge portions 55 engage open stop members defined by the portions 28 of the side edge 27, near the downstream surfaces 26' of the projections 24. When the occluder reaches the fully open position, arm 51'' will bear against side edge 34', thereby arresting further pivotal movement beyond the predetermined range provided by the dimension of the guide member 32. Simultaneously upon reaching this point, each straight edge 55 adjacent the ear 51, having passed over the curved portion 29 of the side edge 29, will engage the upper stop portion 28 of the side edge 27. When the direction of blood flow is reversed, the fluid pressure will be applied to the downstream surface 42 of the occluder causing the pivot ears 51 to undergo reverse rotation in an upstream direction within the guide pockets until the leading edge 47 of the occluder returns to its position of engaged relation with the inclined edge 40 whereby to effectively check the flow of blood in the reverse or upstream direction. Thus, the occluder 12 is caused to pivot within the limits precisely and positively defined by the particular structure of the guide means 32 together with the limit stop means provided in the open position by the projection 24, and in the closed position by the inclined ledge 40.

In the instant embodiment, the occluder is capable of opening to an angle on the order of 75° to 85° with respect to the annular valve body 11. This angle may be suitably adjusted by altering the dimensions of the triangular guide means, i.e., by increasing or decreasing the measurement of the included angle between side edges 34 and 34'; or by altering the location or dimension of the limit stop means on projections 24 of the valve body.

It is an additional advantage of the instant valve arrangement that the pivotal movements of the curved ear 51 and rib 52 within the guide pocket creates a sweeping or wiping action along the concave inner bearing surface, thereby preventing stagnation of blood within the pockets 30. Further to this end, the limit stop is positioned within the guide pocket, and the arcuate edge 56 of the ear is of a length slightly shorter than the diameter of the guide pocket so as to permit the ears 51 to undergo a certain amount of sliding or translatory movement as well as pivotal rotation within the guide pockets as the occluder is caused to open and close. By eliminating a fixed axis or point of rotation between the occluder and the valve body, the unique combination of the T-shaped pivot means and the hemispherical guide pockets allows flow of blood through the guide pockets to effectuate more complete washing action thereof, while nonetheless preventing accidental release of the occluder from the valve body. Moreover, the blood is free to pass to some extent between the surfaces of the occluder and the valve body immediately adjacent the pivot means, particularly between the side edges 27 and the straight edges 55 as well as between the flat facing surfaces 25 of the valve body projections 24 and flat portions 58 of the occluder edge thereby providing a similar washing action between the mating surfaces.

It is therefore to be understood that while a preferred form of the present invention is herein set forth and described, various modifications and changes may be made therein without departing from the spirit and scope of the present invention as defined by the amended claims.

I claim:

1. In an artificial heart valve comprising an annular valve body having an inner circumferential wall surface defining an orifice, and a generally flat occluder supported therein for pivotal movement about an eccentric pivot axis between an open position allowing blood flow through said orifice and a closed position preventing blood flow therethrough, the improvement comprising:

(a) a pair of pivot portions disposed on opposite sides of said inner wall surface and offset with respect to the diameter of said annular valve body, each pivot portion including a shallow concave pocket member defining an inner bearing surface having a limit stop therein, said limit stop being raised with respect to said bearing surface; and (b) occluder retaining means in the form of a pair of lateral extensions on opposite sides of said occluder, each lateral extension being convexly curved along its length for insertion into a concave pocket member for swinging movement along said bearing surface, each said lateral extension further being provided with a rib member curved in a transverse direction with respect to the plane of pivotal movement of said lateral extensions within said pocket members, said lateral extensions engageable with said limit stops to limit the pivotal opening movement of said occluder in response to blood flow through said passageway.

2. In an artificial heart valve according to claim 1, said pivot portions having inner flat wall surfaces intruding from said inner circumferential wall surface into said orifice.

3. In an artificial heart valve according to claim 1, each of said pocket members having inner bearing surfaces of generally spherical configuration.

4. In an artificial heart valve according to claim 3, each said limit stop being in the form of a generally triangular segment raised with respect to said bearing surface.

5. In an artificial heart valve according to claim 1, said lateral extensions inset with respect to outer peripheral edges of said occluder.

6. In an artificial heart valve according to claim 1, including an inclined ledge projecting radially inwardly from said inner wall surface along a portion thereof engageable with said occluder when said occluder is in the closed position, and sidewall portions on said intruding planar portions of said inner wall surface engageable with said occluder in the open position.

7. In an artificial heart valve comprising an annular valve body having an inner circumferential wall surface defining a generally circular passageway, and at least one generally circular planar occluder supported therein for pivotal movement on an eccentric pivot axis between an open position allowing blood flow through said passageway and a closed position preventing blood flow therethrough, the improvement comprising:

cooperative guide means including:

(a) spaced opposed planar portions intruding into said passageway from said inner wall surface and offset with respect to the diameter of said annular valve body to define said eccentric pivot axis, each planar portion including a concave pocket member having a generally triangular guide member therein, said guide member being raised with respect to said pocket member and having side edges converging in a direction toward the center of said pocket member;

(b) occluder support means in the form of a pair of planar lateral extensions disposed in recessed areas on opposite sides of said occluder, each said lateral extension being convexly curved along its length for insertion into an aligned said pocket member for pivotal movement therein between said converging side edges of said guide members, each said lateral extension further being provided on an upstream side thereof with a generally radially extending rib having a surface curved in a direction transverse with respect to the plane of pivotal movement of said extensions within said pocket members; and means on said annular valve body comprising an inclined ledge projecting radially inwardly from said inner wall surface along a portion thereof engaging said occluder when said occluder is in the closed position, and sidewall portions on said intruding planar portions of said inner wall surface engaging the upstream surface of said occluder in the open position whereby to limit the pivotal opening movement thereof in response to blood flow through said passageway.

8. In an artificial heart valve according to claim 7, each of said pocket members having a concave depression of generally spherical configuration.

9. In an artificial heart valve according to claim 8, each said lateral extension having a length less than the diameter of said bearing surface of said pocket member in which it is disposed.

10. In an artificial heart valve according to claim 7, each said rib having a longitudinally curved surface corresponding to the spherical configuration of its associated pocket member.

11. In an artificial heart valve according to claim 7, each said lateral extension and associated rib being of generally T-shaped cross-sectional configuration.

12. In an artificial heart valve according to claim 7, said occluder having an outer peripheral edge corresponding to said circular passageway formed by said inner circumferential wall surface, and each said occluder support means disposed within said outer peripheral edge of said occluder.

13. In an artificial heart valve according to claim 11, each of said lateral extensions formed by a sharp angulation of said peripheral edge radially inwardly toward the center of said occluder to define straight edges substantially parallel to said eccentric pivot axis which are offset with respect to the diameter of said occluder.

14. In an artificial heart valve according to claim 13, each of said straight edges being rounded in cross-section and merging into each said lateral extension in the plane of said occluder.

* * * * *